US010143505B2

United States Patent
Bardají Pascual (10) Patent No.: US 10,143,505 B2
(45) Date of Patent: Dec. 4, 2018

(54) DEVICE FOR USE IN SURGICAL TREATMENT OF FUNNEL CHEST AND METHOD OF TREATMENT

(71) Applicant: CORPORACIÓ SANITÀRIA PARC TAULÍ, Sabadell (Barcelona) (ES)

(72) Inventor: Carlos Bardají Pascual, Sant Cugat del Vallés (ES)

(73) Assignee: CORPORACIO SANITARIA PARC TAULI, Sabadell (Barcelona) (ES)

( * ) Notice: Subject to any disclaimer, the term of this patent is extended or adjusted under 35 U.S.C. 154(b) by 0 days.

(21) Appl. No.: 14/294,093

(22) Filed: Jun. 2, 2014

(65) Prior Publication Data

US 2014/0350613 A1 Nov. 27, 2014

Related U.S. Application Data

(63) Continuation of application No. 13/059,632, filed as application No. PCT/EP2009/060605 on Aug. 17, 2009, now Pat. No. 8,777,952.

(30) Foreign Application Priority Data

Aug. 19, 2008 (EP) .................................... 08162587

(51) Int. Cl.
*A61B 17/80* (2006.01)
*A61B 17/86* (2006.01)

(52) U.S. Cl.
CPC ...... *A61B 17/8076* (2013.01); *A61B 17/8685* (2013.01)

(58) Field of Classification Search
CPC ............ A61B 17/1691; A61B 17/8076; A61B 17/823; A61B 17/80; A61B 17/8004;
(Continued)

(56) References Cited

U.S. PATENT DOCUMENTS 4,327,715 A    5/1982   Corvisier
5,217,462 A    6/1993   Asnis et al.
(Continued)

FOREIGN PATENT DOCUMENTS

CN    2748040 Y  *  12/2005  ............ A61B 17/56
EP    0583520 A1     2/1994
(Continued)

OTHER PUBLICATIONS

Katsumasa Takagi, et al., "The Funnel Chest Correction Method using Zimmer Osteosynthetic Plates", Department of Orthopaedic Surgery, Kumamoto University Medical School, 1984 (the year of publication is sufficiently earlier than the effective U.S. filing date and any foreign priority date so that the particular month of publication is not in issue) pp. 196-199, Kumamoto City, Japan.
(Continued)

*Primary Examiner* — Kevin T Truong
*Assistant Examiner* — Tracy Kamikawa
(74) *Attorney, Agent, or Firm* — Edell, Shapiro & Finnan, LLC (57) ABSTRACT

A device (1) for use in the surgical treatment of a patient suffering from funnel chest characterized in that it comprises a plate adapted to be fitted underneath the skin of the patient, and further characterized in that, in use, said plate can be attached to the patient's sternum and the curvature, length and width of the plate being such that the plate extends on both sides of the sternum and on the outside of the patient's thorax and is supported by the ribs to hold up the sternum.

8 Claims, 12 Drawing Sheets

(58) Field of Classification Search
CPC ............ A61B 17/8014; A61B 17/8019; A61B 17/8061; A61B 17/84; A61B 17/8665; A61B 17/8685; A61B 17/8695
USPC .......... 606/57, 86 R, 280–299, 324, 328, 90, 606/101, 105, 86 A, 86 B, 902–906, 915
See application file for complete search history.

(56) References Cited

U.S. PATENT DOCUMENTS

| | | | | |
|---|---|---|---|---|
| 5,722,976 | A | * | 3/1998 | Brown ............... A61B 17/8076 606/281 |
| 6,007,538 | A | | 12/1999 | Levin |
| 7,052,499 | B2 | * | 5/2006 | Steger et al. ................. 606/291 |
| 7,060,067 | B2 | * | 6/2006 | Needham ........... A61B 17/8869 606/295 |
| 2004/0117016 | A1 | | 6/2004 | Abramson |
| 2004/0260289 | A1 | * | 12/2004 | Padget ................... A61B 17/88 606/67 |
| 2005/0049595 | A1 | * | 3/2005 | Suh .................... A61B 17/7059 606/71 |
| 2005/0187555 | A1 | | 8/2005 | Biedermann et al. |
| 2005/0216010 | A1 | * | 9/2005 | Michelson ...................... 606/69 |
| 2006/0074448 | A1 | | 4/2006 | Harrison et al. |
| 2007/0173842 | A1 | * | 7/2007 | Abdou ............... A61B 17/7059 606/255 |

FOREIGN PATENT DOCUMENTS

| | | |
|---|---|---|
| JP | 0690962 A | 4/1994 |
| WO | WO2004/028412 A1 | 4/2004 |
| WO | WO2005055844 A1 | 6/2005 |

OTHER PUBLICATIONS

International Search Report of the International Searching Authority. International Application No. PCT/EP2009/060605, issued by the European Patent Office, dated Oct. 2, 2009, pp. 1-3; Rijswijk NL.

K. Takagi and M Yamaga, "A New, Modified Operation for Funnel Chest Using the Zimmer Osteosynthetic Plate", Archives of Orthopaedic and Traumatic Surgery, Jun. 1986, vol. 105, Issue 3, pp. 154-157, Springer-Verlag, Berlin Germany.

Joachim Prein et al., "Manual of Internal Fixation in the Cranio-Facial Skeleton: Techniques as recommended by the AO/ASIF-Maxillofacial Group" AO Publishing, 1998 (the year of publication is sufficiently earlier than the effective U.S. filing date and any foreign priority date so that the particular month of publication is not in issue), Chapter 1, p. 24, Springer-Verlag Berlin Heidelberg , Berlin Germany.

* cited by examiner

DEVICE FOR USE IN SURGICAL TREATMENT OF FUNNEL CHEST AND METHOD OF TREATMENT

The invention refers to a device for use in the surgical treatment of funnel chest.

Funnel chest (also known as pectus excavatum or cobbler's chest) is a deformity of the chest, which has a caved-in (or sunken) appearance. It is caused by abnormal growth of the sternum and several ribs. Patients suffering from funnel chest may experience any of the following problems: psychological problems (due to the clearly visible cosmetic imperfection), pain in the chest and back, respiratory problems and cardiac problems.

The respiratory and cardiac problems are due to the fact that the heart is in a slightly different position due to the caved-in thorax than in a normal chest (in which the heart is positioned behind the sternum). Because the heart is in a slightly different position, the lungs may not develop to their appropriate size.

Patients with funnel chest are usually treated surgically. Traditionally, the surgery was performed using the so-called Ravitch technique. This procedure involves removing the cartilage that connects the sternum to the ribs and thus completely detaching the sternum from the ribs. A bar is then introduced behind the sternum to hold it up. The bar is left implanted in the patient's thorax and is only removed when the cartilage has grown back. The Ravitch technique is not widely practiced anymore because it is very invasive, very painful and leaves considerable scarring. It may still be used when other options are unsuccessful (For example, with older patients, whose sternum has calcified.)

Subsequently, the Nuss procedure was developed. The Nuss procedure is much less invasive in that it involves inserting one (or more) concave steel bar(s) into the chest, underneath the sternum. In surgery, the bar is flipped to a convex position. This forces the sternum outwardly, thus correcting the deformity. Stabilizers on either end of the bar(s) may be inserted to avoid flipping (back) of the bar after the operation. E.g. WO 2005/055844 discloses a hoop comprising a stabilisation plate at one of its ends to stabilize the hoop on one side of the sternum. WO 2004/028412 discloses a similar device.

In order to safely carry out the Nuss procedure, the surgeon makes a small incision on the side of the chest, through which a camera, a thoracoscope, enters the body. Images from this camera assist the surgeon in safely performing the operation. The bar can stay in the body for a couple of months up to a number of years. When the bones have solidified into place, the bar is removed. The Nuss procedure is generally less painful than the Ravitch technique and leaves less scarring. On the other hand, it is still very painful for many patients and the operation is not without risk, since a bar is introduced behind the thorax, in the area of the heart and lungs. Additionally, there exists a small risk in that the bar moves after insertion which causes the need for a second surgery.

US 2004/0117016 discloses an apparatus for "Pectus Carinatum". Said apparatus comprises a bar and a plate at either end of the bar (one plate on each side of the sternum).

Additionally, it is known, from CN 2748040Y, to apply a therapeutic treatment, instead of a surgical treatment. A patient is treated by wearing a corset-like device on the outside of the thorax. The document describes a curved plate which is fitted around a patient's chest and comprises a screwing mechanism. The screwing mechanism is screwed into and fixed in the patient's sternum. Over a period of time, using the screwing mechanism, the sternum is gradually raised. The invention in this document is especially designed for the treatment of poor children, whose families cannot afford to pay for a conventional surgery. The disadvantage of this therapeutic device (and similar ones) however is that for a long period (e.g. a 150 days is mentioned in CN2748040), a patient has to carry a device around his/her chest, which is uncomfortable and clearly visible even through clothing, because parts stick out. Additionally, periodically adjusting the screw to raise the chest a bit is painful and it is impractical to use medication such as painkillers for such a prolonged period of time.

There thus still exists a need to improve the surgical treatment of funnel chest, which is less risky, has fewer complications and is less painful. The present invention provides a device for use in the surgical treatment of funnel chest which provides at least some of these advantages.

The present invention namely provides a device for use in the surgical treatment of a patient suffering from funnel chest characterised in that it comprises a plate of substantially continuous curvature and adapted to be fitted underneath the skin of the patient, further characterised in that, in use, said plate can be attached to the patient's sternum and the curvature, length and width of the plate are such that the plate extends on both sides of the sternum and can be fitted on the outside of the patient's thorax and supported by the ribs to hold up the sternum.

The device is positioned around the patient's thorax in surgery. Since it is fitted on the outside of the thorax, the surgeon does not need to enter the area of heart and lungs with the device, so there is less danger during the operation. Since the plate is wide and is fitted around the thorax, it cannot displace after the operation, so that a corrective second operation will not be needed. The curvature of the plate may in some embodiments be substantially continuous. In other embodiments, the plate may be substantially completely straight. In yet other embodiments, the plate may be almost completely straight, and only the end portions are curved to adapt to the shape of the thorax. There are no parts that stick out that are clearly visible, even through clothing. After the thorax has been raised to its desired shape using some kind of lifting means, the device is attached to the sternum through fastening means, e.g. bone screws. The lifting means can then be removed and do not need to stay on the patient's body. The thickness and material of the device are chosen such that it can be fitted under the skin of the patient (but still on the outside of the thorax). Because of the plate's fit on either side of the thorax, the ribs give support to the plate so that it can hold up the sternum. Materials that are suitable include titanium, stainless steel and ceramic materials. In some embodiments, biodegradable polymer materials may also be used. The plate naturally needs to be thick enough to be able to withstand the forces it is subjected to in use. In an aspect of the invention, the thickness of the plate may be between approximately 1 mm and approximately 5 mm. In some embodiments, the thickness may e.g. be 2.5 or 3.5 mm.

Preferably, the plate is provided with at least one hole which is adapted to accommodate a tool used in lifting the patient's sternum. A hole may be provided to accommodate a tool, such as a screw, to bring the chest closer to the device and in the process raise the chest to the desired position. Raising the chest in this way is more gradual and less aggressive than flipping a concave bar to a convex position, as in the Nuss procedure. It will therefore in general be less painful. A single hole adapted to accommodate a tool used in lifting may be provided, but the plate may also be provided with more holes (such as for example two or three). If more than one hole is provided, the force of lifting may be divided over more points. Also, depending on the patient's thorax and depending on the particular chest deformity, it may be easier for a surgeon to lift the sternum using more than one hole and more than one lifting mechanism.

Optionally, the plate comprises additional holes adapted to accommodate fasteners for fastening the plate to the patient's sternum. Preferably bone screws may be used to attach the plate to the sternum. For this purpose, the central part of the device, which in use will be positioned on top of the sternum, may comprise holes to accommodate these screws. It is also possible that the hole(s) used for lifting the sternum may subsequently be used for fastening.

Optionally, the plate comprises a central part, which in use is positioned on top of the sternum, and two side parts, which in use are positioned on the sides of the thorax, the width of the central part and side parts being substantially the same along the length of the plate. The plate comprises distinguishable parts, a central part which is positioned on top of the sternum and side parts which are positioned on either side of the sternum. The fact that the plate comprises various distinguishable parts does not mean that they are physically separable components. The parts are merely indicated to help describe some suitable shapes of the device. A first embodiment may have a substantially constant width along the length of the plate. This shape is the easiest to manufacture and the easiest to handle during surgery. On the other hand, it may not be comfortable for all patients since the surface of the side parts that press on the thorax in this embodiment is relatively small. These parts have to hold and support the sternum after surgery by pressing on the thorax. The local pressure at the sides on the patient's ribs may therefore be slightly painful.

Optionally, the central part of the device is wider than the side parts. If the central part is wider, it covers more of the patient's sternum, so that fastening means may be provided along an increased part of the sternum, more securely fixing the device to the sternum. Also or alternatively, in the central part, more than one hole for accommodating lifting means may be provided.

Optionally, the side parts comprise substantially vertically extending legs at their ends. One option for avoiding the pain due to high pressure at the side parts is to provide the ends of these side parts with substantially vertically extending legs. The surface of the parts of the plate that press on the ribs is increased, which lowers the local pressure. Carrying the plate will thus be less painful for patients. Optionally, these vertically extending legs comprise horizontal extensions at their ends. The horizontal extensions further increase the surface and additionally, may improve the support on the sides of the thorax.

Optionally, the plate comprises a central part, which in use is positioned on top of the sternum, and four side parts, which in use are positioned on the sides of the thorax, the four side parts extending substantially diagonally. This shape can also provide a good fit around the thorax able to support the sternum.

Preferably, the device comprises at least one hole along its surface for improving the attachment of skin around the plate. The plate is positioned underneath the skin and the skin thus has to attach itself on the outside of the plate from the edges of the plate covering it entirely. If one hole or a plurality of holes is provided along the plate's surface, these local points help the skin to attach itself better to the plate.

Preferably, the plate comprises ridges along its width on the side of the plate which in use is directed toward the inside of the patient's body. The plate is adapted to be fitted on the outside of the thorax, which in itself is a secure and stable fit. Locally providing ridges along the width of the plate can help to stabilise the plate in position.

Preferably, the surface of each end region of the device is provided with extra roughness on the side of the plate which in use is directed towards the inside of the patient's body. The roughness on the ends on either side of the sternum may help to more securely fix the plate on the thorax. In this aspect of the invention, the plate will be more stable during the surgery as well.

In another aspect, the present invention provides a kit for use in the surgical treatment of a patient suffering from funnel chest comprising a device according to the invention and means for lifting the sternum. The lifting means may be adapted in size and shape to the device. Suitable lifting means may comprise a screwing mechanism. The lifting means may also be adapted to subsequently function as fastening means.

Optionally, the kit further comprises fastening means for fastening the device to the patient's sternum. Optionally, the lifting means is a screw comprising two separable parts. If such a screw is used, after the sternum has been lifted, the part on the outside of the thorax may be disconnected from the other part, which immediately serves as a fastening means.

These and further possible embodiments of the invention and their advantages will be explained, only by way of non-limiting example, with reference to the appended figures, in which:

FIG. 1, which is defined by sub-part FIGS. 1a, 1b and 1c (no discrete FIG. 1 appearing apart from the sub-parts 1a, 1b and 1c), shows a preferred embodiment of the device according to the invention.

FIG. 2, which is defined by sub-part FIGS. 2a and 2b (no discrete FIG. 2 appearing apart from the sub-parts 2a and 2b), shows a device according to the invention in use during surgery.

Figure 1A:
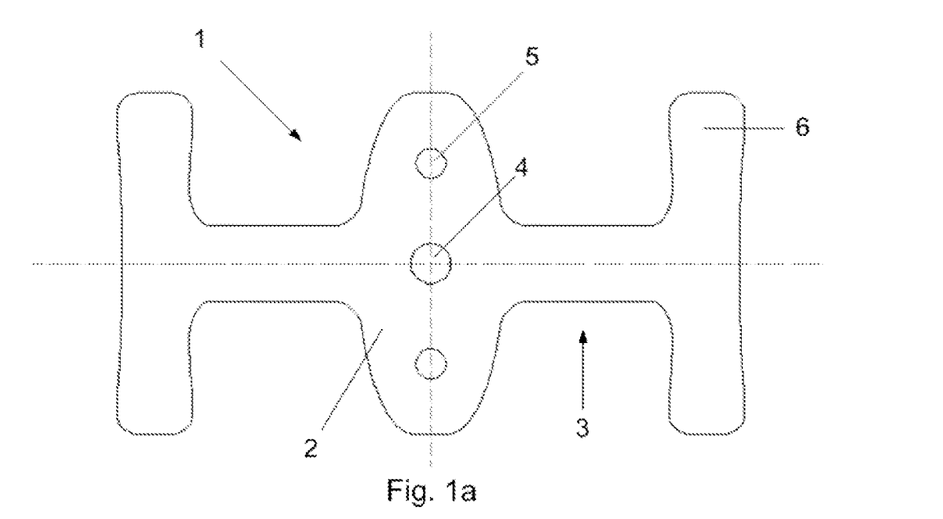
FIG. 1a shows a top view.
Figure 1B:
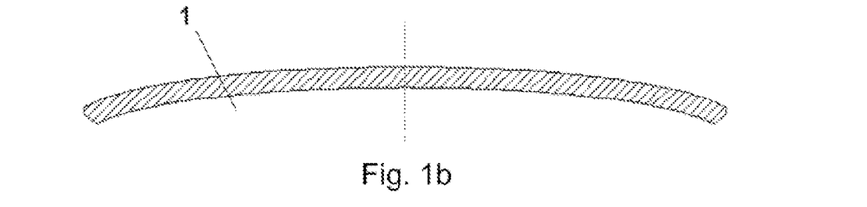
FIG. 1b shows a cross-section and FIG. 1c shows a bottom view.
Figure 1C:
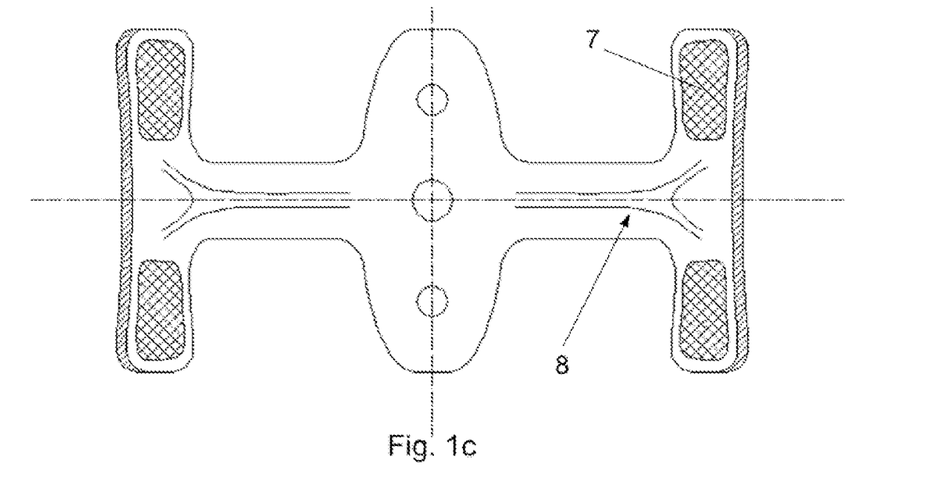

FIG. 1a shows a top view of a preferred embodiment of the device according to the invention. It shows the side of the device which is directed outwardly when fitted on a patient's chest. FIG. 1c shows the opposite side (the side which in use is directed towards the patient's thorax) of the same device. FIG. 1b shows a cross-section of the same device.

The device (1) comprises a central part (2) which supports the sternum and two side parts (3) which are positioned on the thorax. Hole (4) can accommodate a lifting means, such as a screwing mechanism for lifting the sternum. Once the sternum has been lifted to the desired position, fasteners can be attached at holes (5). Within the scope of the invention, it is also possible that more than one hole (4) for accommodating the lifting means is provided. Additionally, it is also possible that the hole (4) which accommodates lifting means, may be used for accommodating a fastener once the sternum has been raised to the desired position.

In the embodiment shown in FIG. 1 (as defined by sub-part/counterpart sub-FIGS. 1a, 1b and 1c (no discrete FIG. 1 appearing apart from these sub-parts)), it can be seen that the central part (2) is enlarged with respect to its adjacent side parts (3). The side parts (3) comprise legs (6) extending vertically at their ends. These legs (6) increase the surface of the device on the sides of the thorax, such that local pressure is limited and the patient experiences less discomfort.

As can be seen in FIG. 1b, the device (1) is curved in such a way that it can be tightly-fitted on a patient's thorax. A correct fit is necessary so that the thorax can support the plate which in turn has to support the sternum (and at the same time, the device is located under the skin of a patient). In the embodiment of FIG. 1b, the plate has a substantially continuous curvature. In other embodiments of the invention, the plate may be substantially completely straight. In yet other embodiments, the plate may be straight with slightly curved end portions on either side to adapt to the local shape of the thorax.

FIG. 1(c) shows the opposite side of the device (1) (which in use is directed towards the thorax of the patient). Patches with increased roughness (7) have been provided on the distal ends of legs (6) for increasing the fit of the device on the chest. For this same purpose, ridges (8) (local protrusions) have been provided along the width of the device.

Figure 2A:
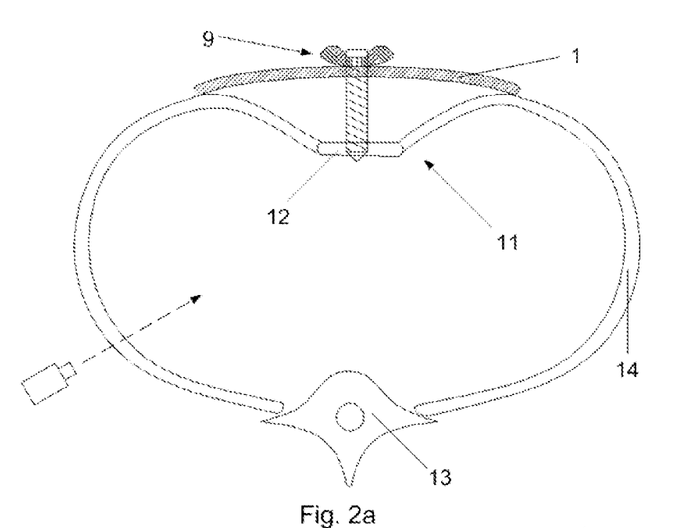
FIG. 2a shows the device before correction of the thorax' shape and FIG. 2b shows the device after the correction.
Figure 2B:
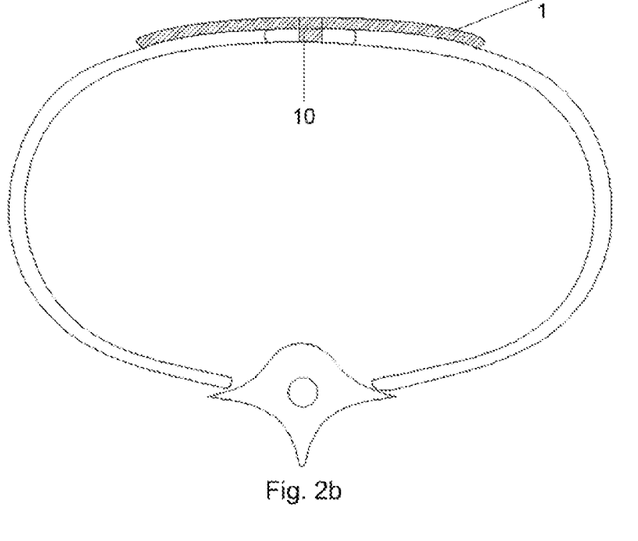

FIG. 2 (as defined by sub-part/counterpart sub-FIGS. 2a and 2b (no discrete FIG. 2 appearing apart from these sub-parts)) shows a cross-section of the thorax of a patient suffering from funnel chest (11). The patient's sternum (12), vertebra (13) and rib (14) have been schematically indicated.

Before the surgery is carried out, measurements of the thorax have to be taken to determine the size of the thorax. The size and shape of the thorax determine the length, width, and curvature of the device (1). Length, width and curvature will have to be determined in such a way that the device fits on the outside of the thorax and that in use the ribs give enough support. Naturally, the exact size and shape of the thorax will be different for every patient. This does not necessarily mean that for every patient, a custom made device of the appropriate size has to be manufactured. In practice, it may be sufficient to provide a number of standard sizes of the device. The surgeon then has to choose the best fitting device for each patient. In practice, it may also be that the plate is completely straight before the surgery starts. After taking the measurements, the plate may be deformed so as to assume the needed curvature.

For most patients, the length of the device will be between approx. 12 cm-20 cm and the width will be between approx 5-10 cm. However, the exact dimensions of the device will depend on the size of the thorax of the patient (and thus e.g. on the age of the patient when surgically treated). Devices with dimensions smaller than these ranges may e.g. be used for younger patients. And devices with dimensions greater than these ranges may be useful for certain patients with a thorax of increased size.

In surgery, a small incision is made on the patient's chest, through which the device (1) is inserted under the skin. The device is then fitted on the outside of the patient's thorax. A lifting mechanism (9) is then used to lift the sternum to its desired position. In this case shown in FIG. 2 (as defined by sub-FIGS. 2a and 2b), a screw and nut are used as lifting means. Optionally, a bushing (or threaded insert) is positioned in the hole in the sternum to accommodate the screw. In this figure, a screw is used, but within the scope of the invention, other lifting means may also be used, such as a suitable bolt. Throughout the procedure, a thoracoscope may be used to provide the surgeon with a view of the inside of the body (as schematically indicated in FIG. 2a). The surgeon can thus make sure that no organs are damaged in the procedure.

After the sternum has been raised to its desired position, the device is fastened to the sternum using one or more fasteners (10). Because of the shape and stiffness of the device, it can withstand the natural tendency of the sternum to go back to its original position.

Figure 3:
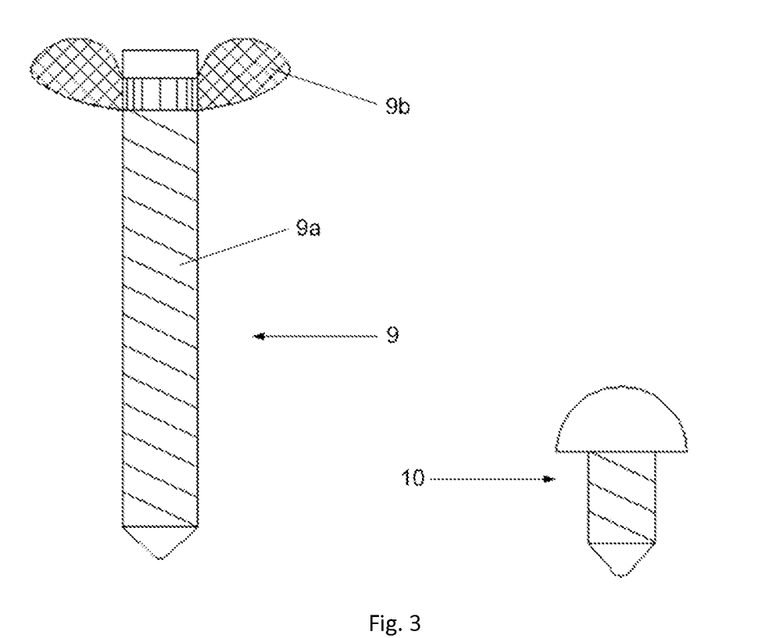
FIG. 3 shows a detail of preferred embodiments of the lifting means and fastening means used in the surgery.

FIG. 3 shows a preferred embodiment of the lifting means (9) and fasteners (10) in more detail. The lifting means (9) in this case consist of a screw (9a) without a head and a wing nut (9b). The fasteners in this embodiment consist in bone screws (10). Alternative lifting means and alternative fasteners may also be used. For example, other types of nuts may be used, such as a hex nut, or a square nut. It may also be that the screw is provided with a hexagon socket in its head, so that it can be manipulated using an Allen key. Other lifting means, such as a suitable bolt may also be used. Additionally it is possible that the lifting means subsequently serves as fastening means. For example, the top part of the screw (9a) may be cut off once the sternum is lifted. The remaining part then serves as fastening means, fixing the sternum to the plate. Another possibility is that the screw (9a) consists of two parts which can be disconnected. Once the sternum has been lifted, the top part which sticks out of the sternum may be disconnected from the bottom part. The bottom part can then serve as fastening means.

Figure 4A:
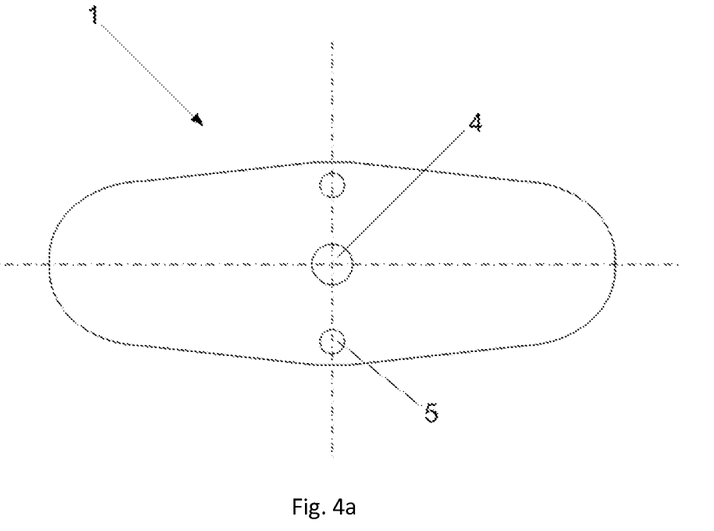
FIGS. 4a-4f show top views of alternative embodiments of the device according to the invention.

FIGS. 4a-4f show various alternative embodiments of the device. (1). They all show a top view. In FIG. 4a, a very simple version of the device is shown. The device (1) according to this figure is very easy to manufacture. It comprises a hole (4) for accommodating lifting means and two holes (5) for accommodating fastening means. In this embodiment, the central part and side parts have a substantially constant width and the various parts are hardly distinguishable. The device essentially forms one continuous plate.

Figure 4B:
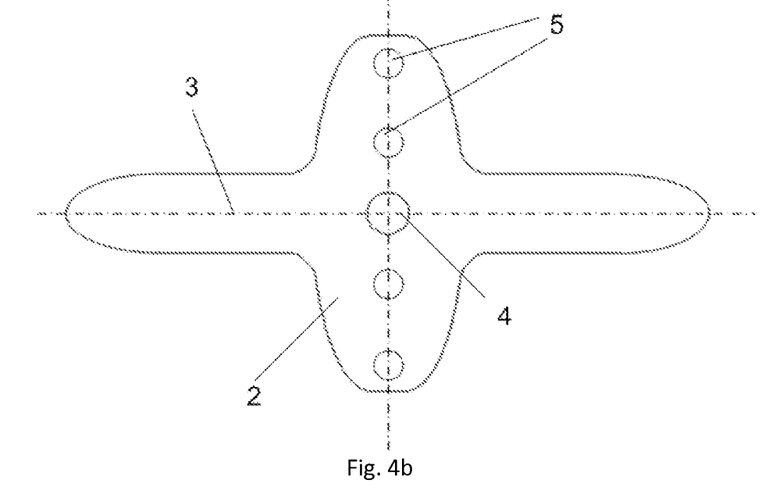

FIG. 4b shows an alternative embodiment, in which a central part (2) and side parts (3) are clearly recognizable. Four holes (5) for accommodating fasteners have been provided in the central part (2).

Figure 4C:
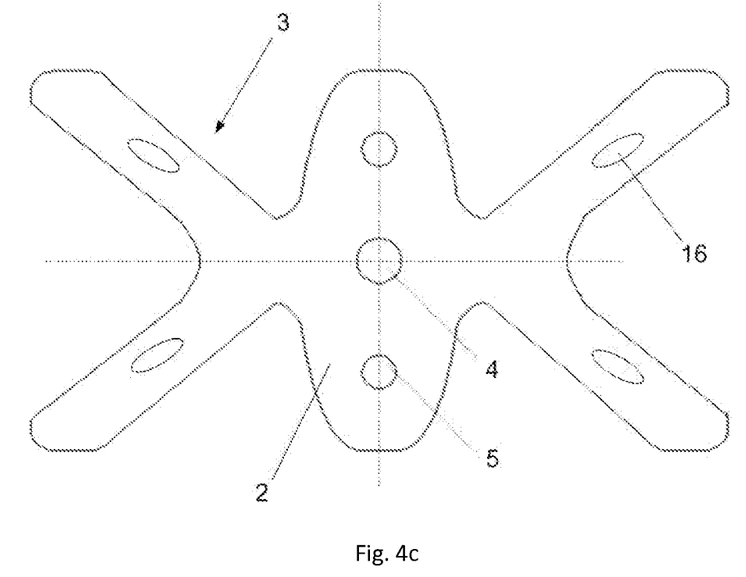

FIG. 4c shows yet another embodiment. In this embodiment, the side parts (3) are formed by four diagonally extending legs. Along the legs, holes (16) are provided for improving the attachment of skin around the plate. Four holes (16) are shown, but it is also possible to provide the device with more or less holes.

Figure 4D:
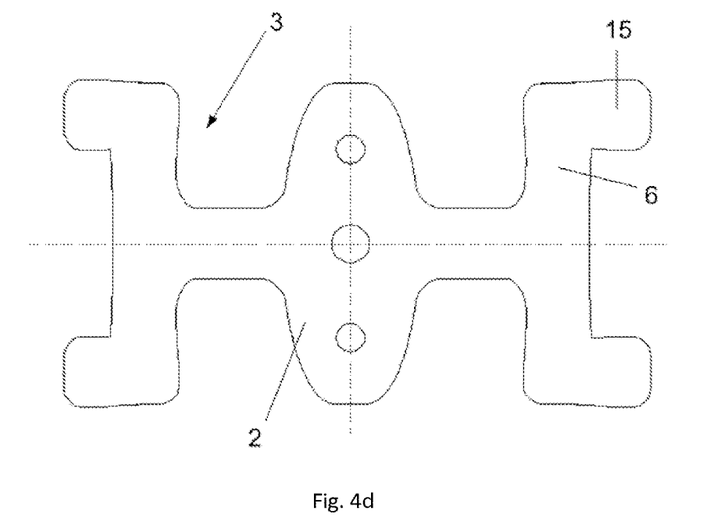

FIG. 4d shows still another embodiment. The side parts (3) comprise substantially vertically extending legs (6) on either end. These vertically extending legs (6) comprise horizontal extensions (15) at their distal ends.

Figure 4E:
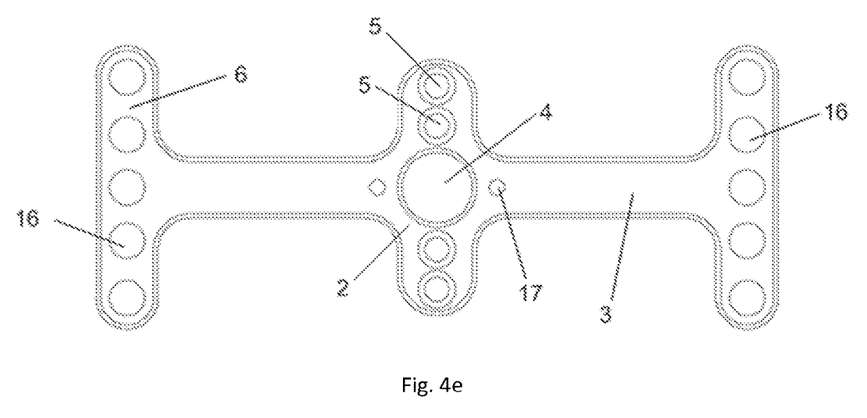

FIG. 4e shows another embodiment of the device. Its shape is similar to the device shown in FIG. 1a. A central part (2) is provided with four holes (5) for fastening the plate to the sternum of a patient. Central hole (4) can accommodate some form of lifting mechanism. Holes (4) and (5) are shown as sunken holes in this embodiment. Fasteners positioned in these holes may comprise sunken heads, so that the fasteners are even less visible from the outside. Five holes (16) for improving the attachment of the skin around the plate are foreseen on vertically extending legs (6). Finally two smaller holes (17) are provided for accommodating a stabilizing tool. In use, when the sternum is being lifted, it may happen that the plate rotates a little bit. To avoid this from happening, a stabilizing tool (later described with reference to FIG. 5e) may be used which can be accommodated in holes (17). In use, while the screw (or bolt or other suitable lifting mechanism) is rotated, the stabilizing tool may be held so that the device is inhibited from rotating. Another way of inhibiting movement of the plate during the surgery may be achieved by proving rough patches along the surface of the plate (as was described with reference to FIG. 1c).

Figure 4F:
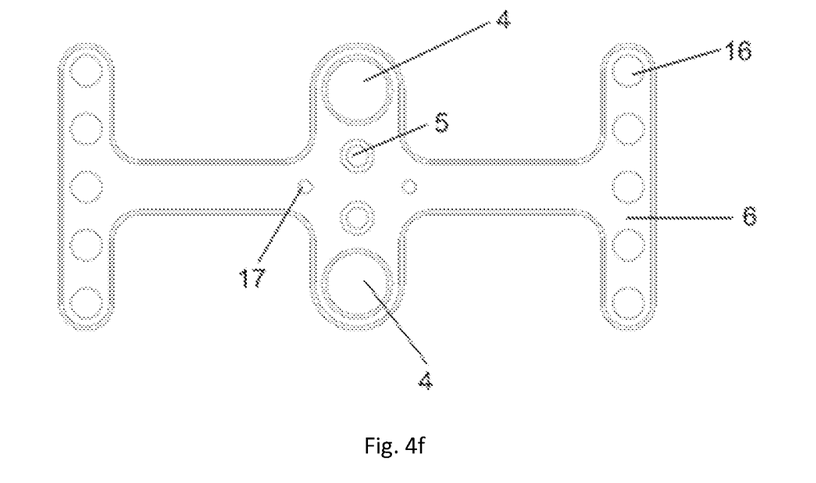

FIG. 4f shows yet another embodiment of the device according to the present invention. The device in this embodiment is very similar to the one shown in FIG. 4e. In this embodiment however, two holes (4) for accommodating two lifting mechanisms may be provided. In some patients, the sternum may have quite an irregular shape. To properly raise the sternum to its desired position, it may be necessary to provide a lifting force at two or more points. For this reason, in the embodiment of FIG. 4f, a plurality of holes (4) is provided. The lifting mechanisms may be the same or different for each of the holes. The size of each of the holes (4) may therefore also be different in some embodiments of the invention.

The embodiments shown in FIG. 4 are not to be interpreted as limiting for the scope of the invention. Features disclosed in the various figures may be combined with each other. In particular, the number of holes (5) accommodating fastening means may be changed in each of the shown embodiments, one hole or a plurality of holes (16) for improving the attachment of the skin may be provided in all shown embodiments, and crests (8) and roughness (7) shown in FIG. 1c may be provided in all embodiments shown in FIGS. 4a-4f.

Figure 5A:
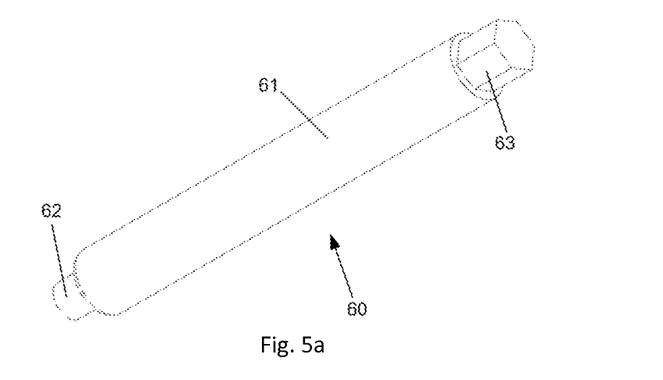
FIGS. 5a-5e show isometric views of various tools that may be used in the system and a method of surgical treatment according to the present invention.

FIGS. 5a-5e show isometric views of various tools that may be used in the system and a method of surgical treatment according to the present invention. FIG. 5a shows a power screw (60) which may constitute part of the lifting mechanism in an embodiment of the present invention. Power screw (60) is externally threaded (61, not shown) and further comprises a bottom part (62), which is also externally threaded (not shown). Power screw (60) in this embodiment furthermore comprises a hexagonal head (63) for its manipulation with a suitable key.

Figure 5B:
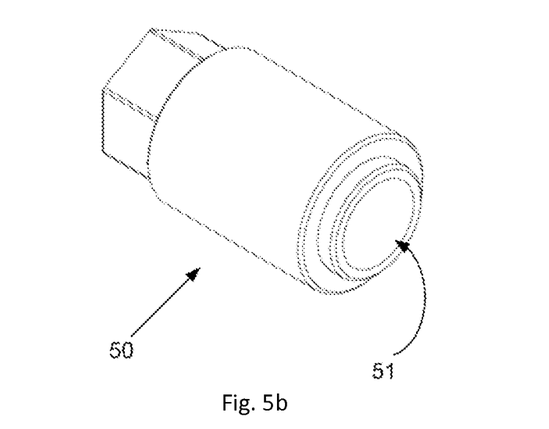

FIG. 5b shows a nut (50), which comprises internal threading (51, not shown). In use, nut (50) may be screwed onto power screw (60). Power screw (60) may then be screwed into a patient's sternum. The nut (50) may then be unscrewed to raise the sternum (as illustrated later with reference to FIGS. 6 and 7).

Figure 5C:
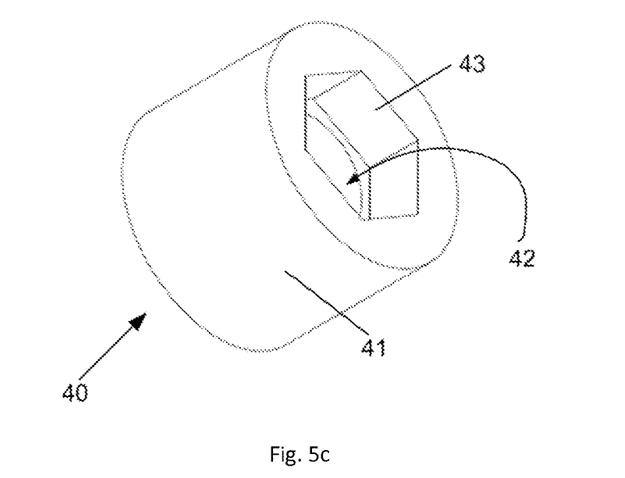

FIG. 5c shows a threaded insert (40) which, in use, may be positioned in a hole drilled in the sternum. The internal threading of the insert may then be used for mating with the threading (62) of the bottom part of screw (60). Insert (40) also is provided with external threading (41, not shown) and comprises a hexagonal socket (43), so that it may be manipulated using a suitable key.

Figure 5D:
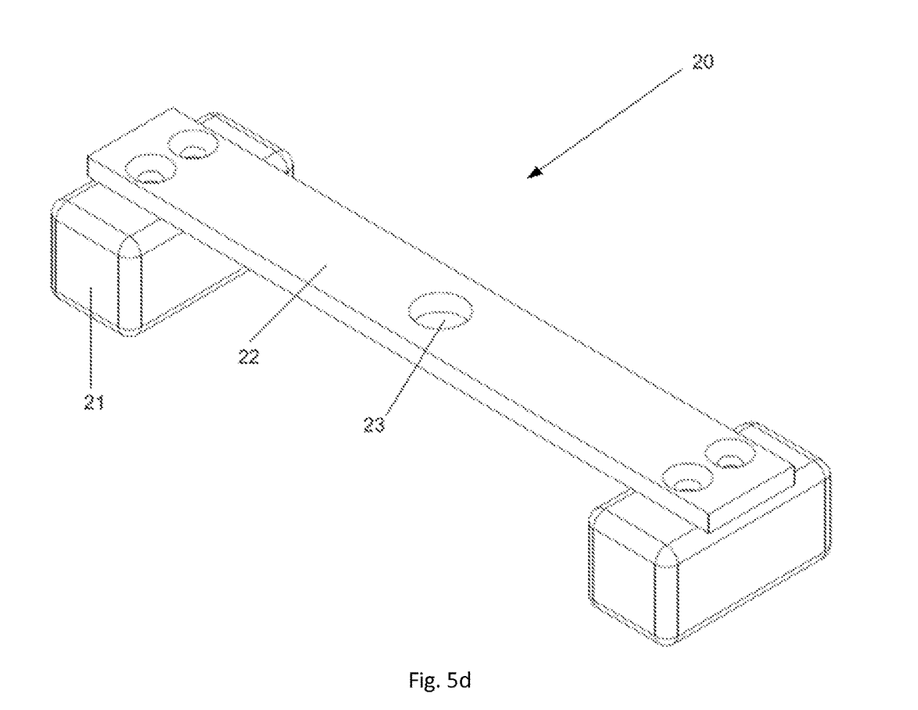

FIG. 5d shows a support tool (20) which may be used advantageously in some embodiments of the invention. Support tool (20) comprises a central section (22) and two side supports (21). Central section (22) is provided with a central hole (23) which can accommodate a lifting mechanism used in the present invention. The use and function of support tool (20) will further be explained with reference to FIGS. 7a and 7b.

Figure 5E:
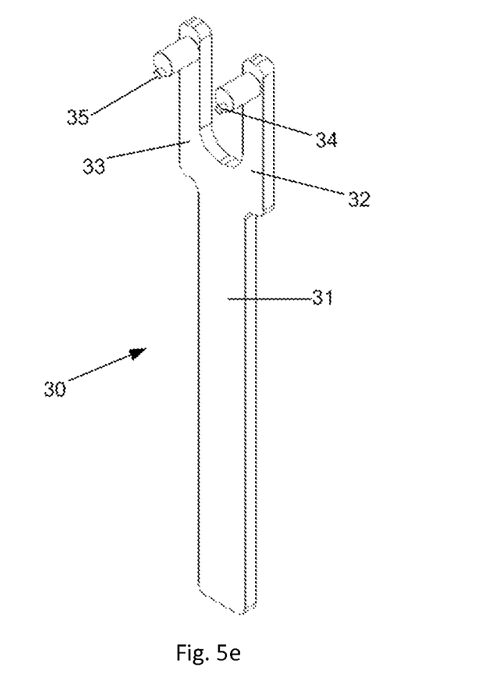

FIG. 5e shows a stabilizing tool (30) which may be used advantageously in some embodiments of the present invention. Stabilizing tool (30) comprises a base (31) which serves as a handle. It furthermore comprises legs (32, 33) at the end of its base. Legs (32, 33) comprise protrusions (34,35) that can engage holes (17) of FIGS. 4d and 4e. By placing the stabilizing tool in such a way that protrusions (34, 35) enter in the holes (17) of the plate, the plate can be stabilized during lifting of the sternum. The surgeon (or assistant) merely needs to hold base (31) while screwing e.g. power screw (60).

FIGS. 6a-6e illustrate a method of surgical treatment using a device according to the present invention. The surgical treatment may comprise making two incisions (A and B) in the patient's chest, see FIG. 6a. Central incision (B) may be used to access the sternum. Through this incision, a hole may be drilled in the patient's sternum. After a hole has been drilled, a suitable tap may be used to create threading in said hole. Device (1) may be introduced through incision (A) and may be rotated to be positioned on top of sternum (12) and the ribs (14), see FIG. 6b.

Figure 6A:
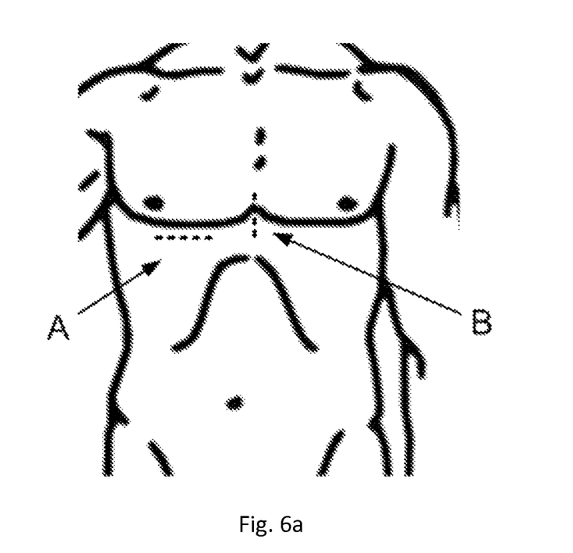
FIGS. 6a-6e illustrate a method of surgical treatment using a device according to the present invention.
Figure 6B:
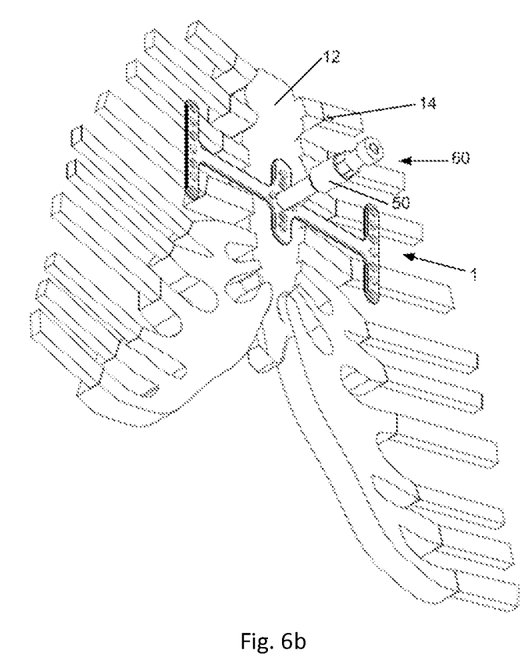
Figure 6C:
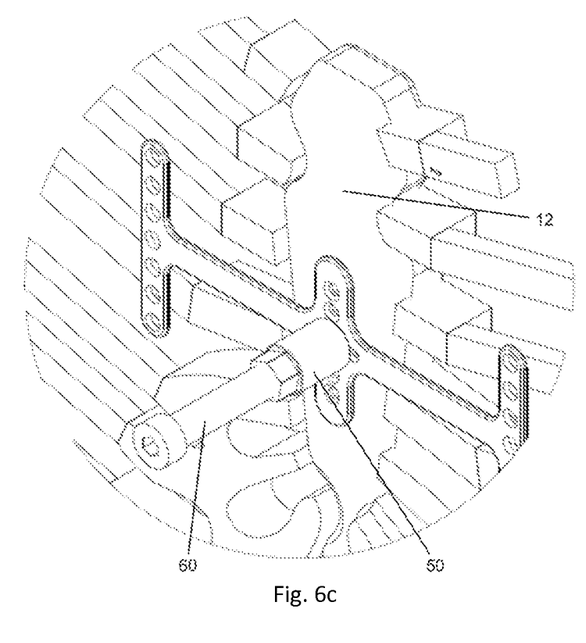

Nut (50) may be screwed onto power screw (60). Subsequently, power screw (60) is screwed into the hole previously drilled in the sternum. Then, to lift the sternum, nut (50) may be unscrewed. In FIG. 6c, nut (50) has been unscrewed to be positioned exactly on top of the plate (without yet raising the sternum). By further unscrewing nut (50), nut (50) will exert a force on plate (1) but the plate cannot be lowered since it is supported by ribs (14). As a consequence, sternum (12) will be raised by further unscrewing nut (50).

Figure 6D:
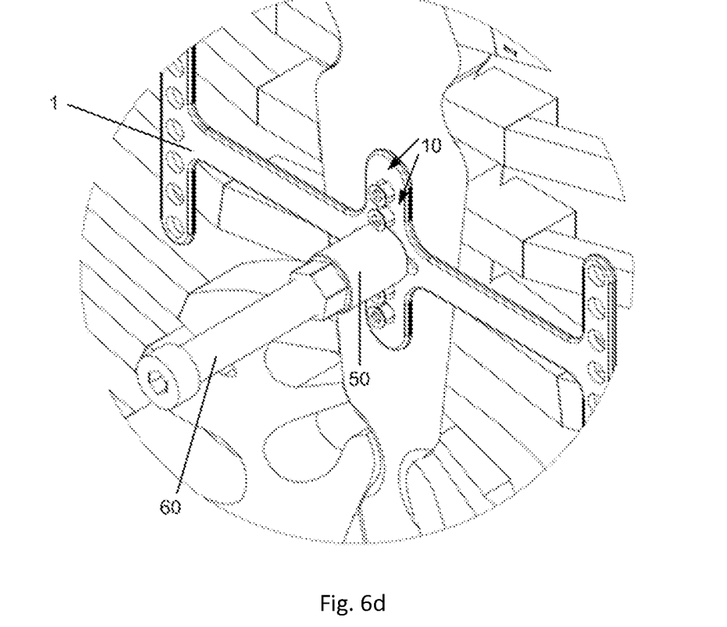

FIG. 6d shows the sternum in its desired position. Fasteners (10) may then be used to fasten plate (1) to the sternum. In the embodiment of FIG. 6d, sunken head screws are used. Subsequently, power screw (60) may be removed by unscrewing it from the hole in the sternum. Finally, the central hole in plate (1) which was used for accommodating power screw (60), may also be used for accommodating a fastener (70) that also connects the sternum to the plate, see FIG. 6e.

Figure 6E:
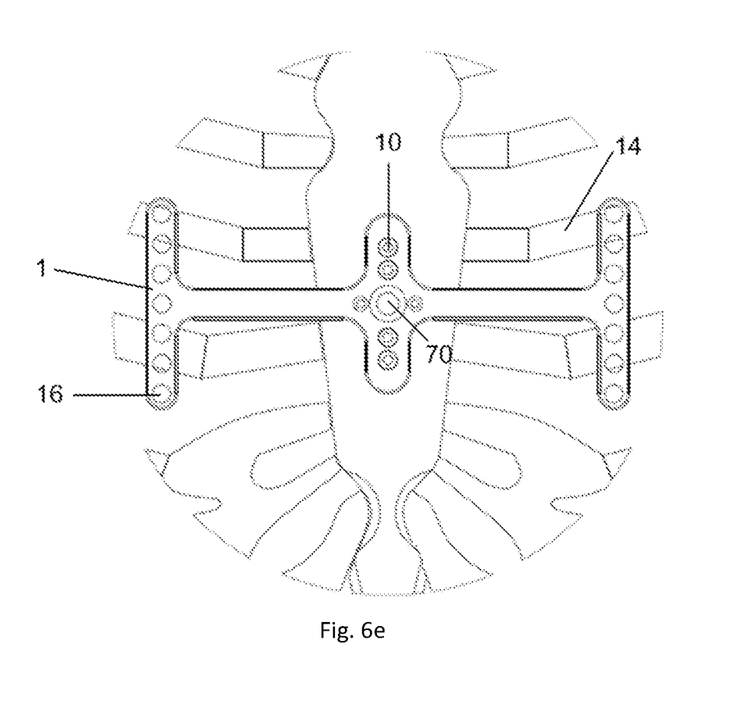

It can be seen in FIG. 6e that the central part of the device (1) is thus fixed to the sternum and the side parts of the device extend on both sides of the sternum, beyond the cartilage. The device is thus supported by the ribs to hold up the sternum.

Figure 7A:
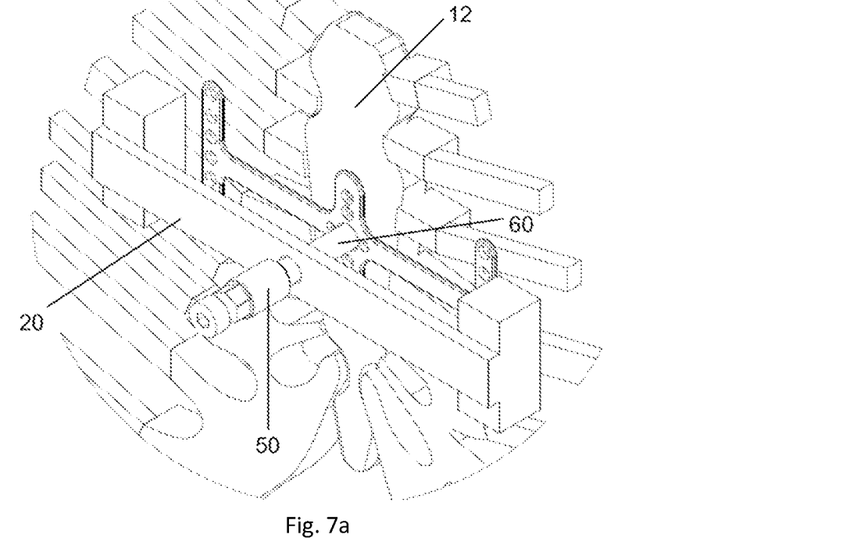
FIGS. 7a and 7b illustrate an alternative method of surgical treatment using a device according to the present invention.
Figure 7B:
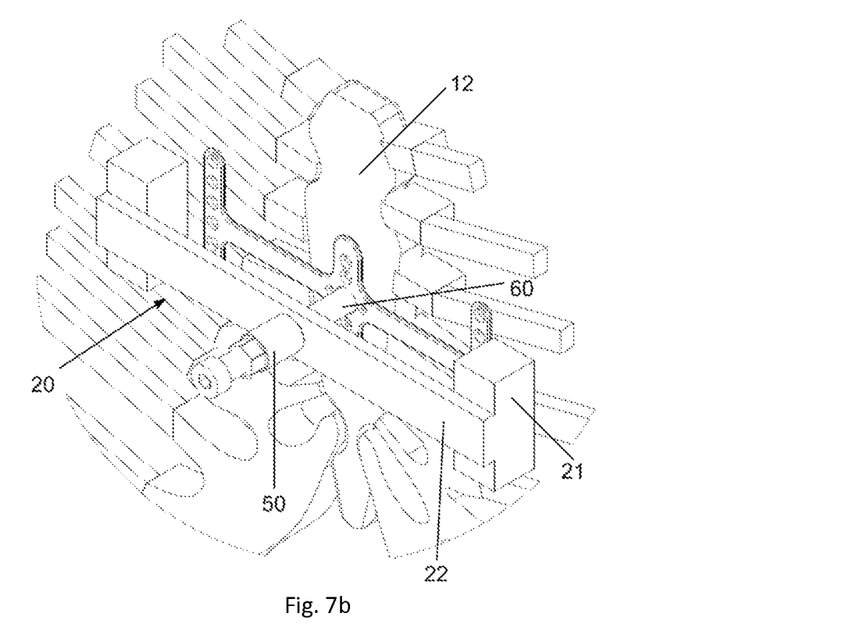

An alternative method of surgical treatment using a device according to the present invention is illustrated in FIGS. 7a and 7b. Before screwing power screw (60) with nut (50) into the hole in the sternum, a support tool (20) may be placed on the patient's chest (on top of the skin). Now, when unscrewing nut (50), nut (50) exercises force on central section (22) of support tool (20) instead of on device (1). Depending on the surgeon's preference, such a support tool (20) may or may not be used in a method of treatment according to the present invention.

Figure 8:
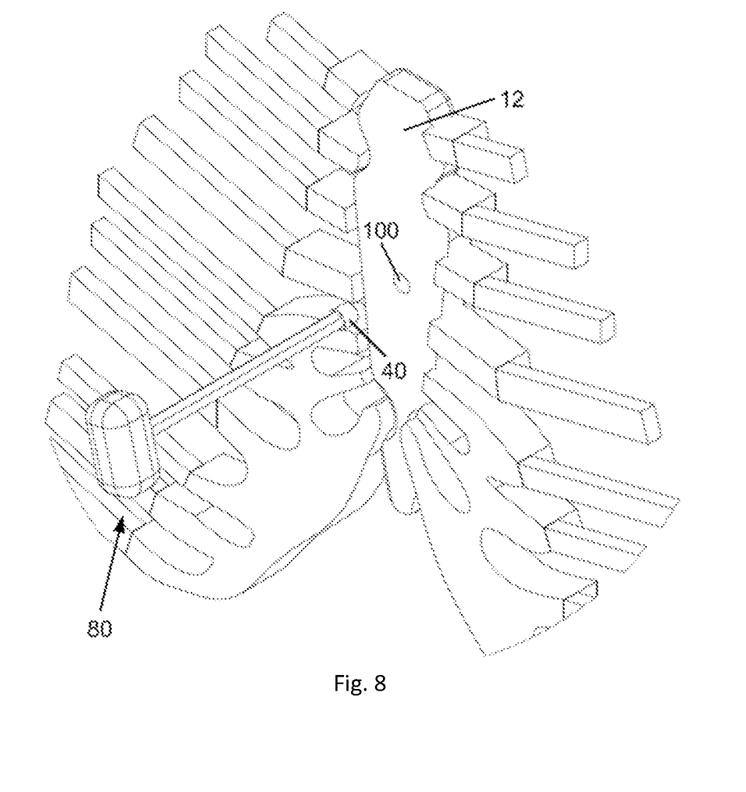
FIG. 8 illustrates an alternative step in the method of treatment according to the present invention.

FIG. 8 illustrates an alternative step in the method of treatment according to the present invention. In some embodiments of the invention, a threaded insert (40) may be inserted into hole (100) previously drilled into the patient's sternum. Such a threaded insert (40) may make it easier to provide for a good threading in the hole (100), which accommodates screw (60). FIG. 8 illustrates that a standard key (80) may be used to position (and screw) threaded insert (40). In case of the threaded insert (40), shown in FIG. 5c, the key (80) would have to comprise a suitable hexagonal head to be introduced into hexagonal socket (43). The same key (80) may of course also be used to remove insert (40) from the hole after the treatment.

For completeness, various aspects of the present invention are set out below in the following numbered clauses:

Numbered Clauses

1. A device for use in the surgical treatment of a patient suffering from funnel chest characterised in that it comprises a plate adapted to be fitted underneath the skin of the patient, further characterised in that, in use, said plate can be attached to the patient's sternum and the curvature, length and width of the plate are such that the plate extends on both sides of the sternum and can be fitted on the outside of the patient's thorax and supported by the ribs to hold up the sternum.
2. A device according to clause 1, characterised in that the plate is provided with at least one hole which is adapted to accommodate a tool used in lifting the patient's sternum.
3. A device according to clause 1 or 2, characterised in that the plate is provided with two or more holes adapted to accommodate a tool used in lifting the patient's sternum.
4. A device according to any previous clause, characterised in that the plate comprises additional holes adapted to accommodate fasteners for fastening the plate to the patient's sternum.
5. A device according to any previous clause, characterised in that the plate is provided with an anti-bacterial agent and/or an anti-allergenic agent.
6. A device according to any previous clause, characterised in that the plate comprises a central part, which in use is positioned on top of the sternum, and two side parts, which in use are positioned on the sides of the thorax, the width of the central part and side parts being substantially the same along the length of the plate.
7. A device according to any of clauses 1-5, characterised in that the plate comprises a central part, which in use is positioned on top of the sternum, and two side parts, which in use are positioned on the sides of the thorax, the central part being wider than the adjacent side parts.
8. A device according to any of clauses 1-5, characterised in that the plate comprises a central part, which in use is positioned on top of the sternum, and two side parts, which in use are positioned on the sides of the thorax, the side parts at their ends comprising substantially vertically extending legs.
9. A device according to clause 8, in which the central part is locally wider than the adjacent side parts.
10. A device according to clauses 8 or 9, in which the substantially vertically extending legs comprise horizontal extensions at their ends.
11. A device according to any of clauses 1-5, characterised in that the plate comprises a central part, which in use is positioned on top of the sternum, and four side parts, which in use are positioned on the sides of the thorax, the four side parts extending substantially diagonally.
12. A device according to any previous clause, characterised in that it comprises at least one hole along its surface for improving the attachment of skin around the plate.
13. A device according to clause 12, characterised in that the plate comprises a plurality of holes along its surface for improving the attachment of the skin around the plate.
14. A device according to any previous clause, characterised in that the plate comprises ridges along its width on the side of the plate which in use is directed towards the inside of the patient's body.
15. A device according to any previous clause, characterised in that at least parts of the surface of the device are provided with extra roughness on the side of the plate which in use is directed towards the inside of the patient's body.
16. A device according to clause 15, characterised in that the end portions of the side parts of the device are provided with extra roughness on the side of the plate which in use is directed towards the inside of the patient's body.
17. A kit for use in the surgical treatment of a patient suffering from funnel chest comprising a device according to any previous clause and means for lifting the sternum.
18. A kit according to clause 17, further comprising fasteners for fastening the device according to any of clauses 1-16 to the patient's sternum.
19. A kit according to clause 17 or 18, wherein the lifting means comprises a screw having two separable parts.
20. A kit according to clause 17 or 18, wherein the lifting means comprise a power screw.
21. A method of treating a patient suffering from funnel chest comprising making an incision in the patient's chest and introducing a plate underneath the skin and on the outside of the thorax, said plate having a curvature, length and width such that the plate extends on both sides of the sternum and can be fitted on the outside of the patient's thorax, lifting the sternum to a desired position, and fixing the sternum to said plate.
22. A method of treating a patient suffering from funnel chest according to clause 21, wherein said plate comprises one or more holes for accommodating a tool used in lifting the sternum.
23. A method of treating a patient suffering from funnel chest according to clause 21 or 22, wherein said plate comprises a plurality of holes for accommodating fasteners for fixing the sternum to said plate.
24. A method of treating a patient suffering from funnel chest according to any of clauses 21-23, wherein at least parts of the surface of the plate are provided with extra roughness on the side of the plate which is directed towards the inside of the patient's body.
25. A method of treating a patient suffering from funnel chest according to any of clauses 21-24 further comprising drilling a hole in the patient's sternum cutting a thread in said hole using a tap.
26. A method of treating a patient suffering from funnel chest according to any of clauses 21-25, wherein lifting the sternum to a desired position comprises positioning a power screw with a nut in a hole in the sternum, and unscrewing the nut from the screw to react against said plate positioned on the thorax, such that the sternum is lifted.
27. A method of treating a patient suffering from funnel chest according to any of clauses 21-25, further comprising positioning a support tool on the patient's thorax, and wherein lifting the sternum to a desired position comprises positioning a power screw with a nut in a hole in the sternum, and unscrewing the nut from the screw to react against said support tool positioned on the thorax, such that the sternum is lifted.
28. A method of treating a patient suffering from funnel chest according to clause 26 or 27, further comprising inserting a threaded insert in the hole in the sternum and wherein, positioning the power screw with a nut in the hole in the sternum comprises screwing the power screw in the threaded insert.

29. A method of treating a patient suffering from funnel chest according to any of clauses 21-28, wherein said plate is stabilized using a stabilizing tool during said lifting of the sternum to a desired position.

The invention claimed is:

1. A kit for use in the surgical treatment of a patient suffering from funnel chest comprising:
a device configured for use in said surgical treatment comprising:
a plate configured to be fitted completely underneath a skin of the patient, and having a substantially central portion configured to be attached to a top surface of a sternum of the patient, the central portion having a bottom side that in use faces towards the sternum and a top side opposite the bottom side that faces away from the sternum, the central portion having a first vertically extending side and a second vertically extending side, the plate having first and second side portions that respectively extend outwardly from the first and second sides of the central portion with there being no other side portions extending outwardly from the first and second sides of the central portion other than the first and second side portions, the first side portion comprising a single first member that extends in a horizontal direction away from the first vertically extending side of the central portion, the second side portion comprising a single second member that extends in a horizontal direction away from the second vertically extending side of the central portion, the first member having at an end thereof a vertically extending first leg, the second member having at an end thereof a vertically extending second leg, the first side portion configured such that when the central portion is attached to the top surface of the sternum the vertically extending first leg extends at least partially across both first and second spaced apart ribs on the first vertically extending side of the central portion of the plate, the second side portion configured such that when the central portion is attached to the top surface of the sternum the vertically extending second leg extends at least partially across both third and fourth spaced apart ribs on the second vertically extending side of the central portion of the plate, the central portion is wider than each of the first and second members, the central portion including a first hole of a first cross-sectional area to accommodate a fastener for attachment of the plate to the patient's sternum and a second hole of a second cross-sectional area, the second cross-sectional area being greater than the first cross-sectional area, each of the first and second holes extending through the top and bottom sides of the central portion of the plate; and
a tool that in use works in conjunction with the plate to lift the patient's sternum toward the bottom side of the central portion of the plate, the tool comprising:
a shaft having a length and being capable of being passed through the second hole, the shaft having external threads, a first portion of the external threads being configured to be directly or indirectly coupled with the sternum to fix the shaft to the sternum; and
a nut having internal threads that cooperate with a second portion of the external threads of the shaft in a manner that causes the nut to translate along the length of the shaft when the nut rotates on the shaft, in use when the nut rotates on the shaft in a first direction, the nut translates along the length of the shaft toward the central portion of the plate, in use when the nut rotates on the shaft in a second direction opposite the first direction, the nut translates along the length of the shaft away from the central portion of the plate, the nut having a surface that is configured to engage with the top side of the central portion of the plate to cause a lifting of the sternum towards the bottom side of the central portion of the plate when the first portion of the external threads are embedded in the sternum and the nut is rotated on the shaft in the first direction.

2. The kit according to claim 1, wherein the plate comprises at least one hole along its surface for improving the attachment of skin around the plate.

3. The kit according to claim 1, wherein the plate comprises ridges along its width on a side of the plate which when in use is directed toward an inside of the patient's body.

4. The kit according to claim 1, wherein the plate is provided with one or both of an anti-bacterial agent and an anti-allergenic agent.

5. The kit according to claim 1, wherein the central portion and the first and second side portions of the plate are integrally formed.

6. The kit according to claim 1, wherein each of the vertically extending first and second legs has one or more through holes.

7. The kit according to claim 6, wherein a central vertical axis of the plate bisects the tool hole and the fastener hole, and a central horizontal axis of the plate bisects the first member and the second member.

8. The kit according to claim 1 further comprising:
an insert having internal threads and external threads, the internal threads of the insert being configured to threadedly engage the first portion of the external threads of the tool shaft to secure the tool to the insert, the external threads of the insert being configured for engagement with a wall of a hole drilled in the sternum of the patient to secure the insert to the sternum.

* * * * *